US00PP37310P2

(12) United States Plant Patent
Guerrero

(10) Patent No.: US PP37,310 P2
(45) Date of Patent: Mar. 10, 2026

(54) HYBRID TEA ROSE PLANT NAMED 'ESM R895'

(50) Latin Name: *Rosa hybrida*
Varietal Denomination: ESM R895

(71) Applicant: GENVIV HOLDINGS, LLC, Miami, FL (US)

(72) Inventor: Maria Elena Guerrero, Quito (EC)

(73) Assignee: GENVIV HOLDINGS, LLC, Miami, FL (US)

( * ) Notice: Subject to any disclaimer, the term of this patent is extended or adjusted under 35 U.S.C. 154(b) by 0 days.

(21) Appl. No.: 19/310,781

(22) Filed: Aug. 26, 2025

(51) Int. Cl.
*A01H 5/02* (2018.01)
*A01H 6/74* (2018.01)

(52) U.S. Cl.
USPC ..... Plt./137

(58) Field of Classification Search
USPC ..... Plt./101, 130, 137
See application file for complete search history.

*Primary Examiner* — Susan Mccormick Ewoldt
(74) *Attorney, Agent, or Firm* — C. Anne Whealy

(57) ABSTRACT

A new and distinct cultivar of Rose plant named 'ESM R895', characterized by its upright and moderately strong flowering stems; moderately vigorous growth habit; glossy dark green-colored leaves; deep pink-colored flower petals and petaloids that become lighter pink in color with development; and excellent postproduction longevity.

1 Drawing Sheet

Botanical designation: *Rosa hybrida.*
Cultivar denomination: 'ESM R895'.

BACKGROUND OF THE INVENTION

The present Invention relates to a new and distinct cultivar of Rose plant, botanically known as *Rosa hybrida*, commercially produced and used as a cut flower Rose plant, and hereinafter referred to by the name 'ESM R895'.

The new Rose plant is a product of a planned breeding program conducted by the Inventor in El Quinche, Pichincha, Ecuador. The objective of the breeding program was to develop new cut flower Rose varieties with unique flower colors and excellent postproduction longevity.

The new Rose plant originated from a cross-pollination made by the Inventor in December 2019 of a proprietary Rose selection identified as line R1104, not patented, as the female, or seed, parent with a proprietary Rose selection identified as line R974, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in August 2021.

Asexual reproduction of the new Rose plant by bud grafting in El Quinche, Pichincha, Ecuador since February 2022 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R895'. These characteristics in combination distinguish 'ESM R895' as a new and distinct Rose plant:

1. Upright and moderately strong flowering stems.
2. Moderately vigorous growth habit.
3. Glossy dark green-colored leaves.
4. Deep pink-colored flower petals and petaloids that become lighter pink in color with development.
5. Excellent postproduction longevity.

Plants of the new Rose differ from plants of the female parent selection in the following characteristics:

1. Flower buds of plants of the new Rose are not as tall as flower buds of plants of the female parent selection.
2. Flower petals of plants of the new Rose are deep pink becoming lighter pink in color whereas flower petals of plants of the female parent selection are red in color.
3. Flower petals of plants of the new Rose are not as thick as flower petals of plants of the female parent selection.
4. Flowers of plants of the new Rose do not open as fully as flowers of plants of the female parent selection.

Plants of the new Rose differ from plants of the male parent selection in the following characteristics:

1. Plants of the new Rose are produce fewer flowering stems per plant per year than plants of the male parent selection.
2. Flower petals of plants of the new Rose are deep pink becoming lighter pink in color whereas flower petals of flowers of plants of the male parent selection are yellow in color.
3. Flowers of plants of the new Rose do not have a detectable fragrance whereas flowers of plants of the male parent selection have a detectable fragrance.
4. Flowers of plants of the new Rose do not open as fully as flowers of plants of the male parent selection.

Plants of the new Rose can also be compared to plants of *Rosa hybrida* 'RUICL1805A', not patented. In side-by-side comparisons, plants of the new Rose differ from plants of 'RUICL1805A' in the following characteristics:

1. Developed stems of plants of the new Rose are dark brownish green in color whereas developed stems of plants of 'RUICL1805A' are dark green in color.
2. Flower buds of plants of the new Rose are narrower than flower buds of plants of 'RUICL1805A'.
3. Flowers of plants of the new Rose have fewer petals than flowers of plants of 'RUICL1805A'.

BRIEF DESCRIPTION OF THE PHOTOGRAPH

The accompanying colored photographic sheet illustrates the overall appearance of the new Rose plant showing the colors as true as it is reasonably possible to obtain in colored reproductions of this type. Colors in the photograph may differ slightly from the color values cited in the detailed botanical description which accurately describe the colors of the new Rose plant.

On the left side of the photographic sheet is a side perspective view of a typical flowering stem of 'ESM R895'.

At the upper right of the photographic sheet is a close-up view of a typical developed flower of 'ESM R895'.

And at the lower right of the photographic sheet are close-up views of the upper and lower surfaces of typical leaves of 'ESM R895'.

DETAILED BOTANICAL DESCRIPTION

The aforementioned photographic sheet and the following observations and measurements describe plants grown in ground beds in a polyethylene-covered greenhouse in Cayambe, Pichincha, Ecuador and produced under typical cut Rose production practices. Plants were grown year round and were 47 months old when the photographs and the description were taken. During the production of the plants, day temperatures ranged from 17° C. to 21° C., night temperatures ranged from 5° C. to 8° C. and light levels averaged 19,338 lux. In the following description, color references are made to The Royal Horticultural Society Colour Chart, 2015 Edition, except where general terms of ordinary dictionary significance are used.

Botanical classification: *Rosa hybrida* 'ESM R895'.

Parentage:

*Female, or seed, parent*.—Proprietary seedling selection of *Rosa hybrida* identified line R1104, not patented.

*Male, or pollen, parent*.—Proprietary seedling selection of *Rosa hybrida* identified line R974, not patented.

Propagation:

*Type*.—By bud grafting.

*Time to initiate roots, summer*.—About seven to ten days at temperatures about 26° C. to 30° C.

*Time to produce a rooted young plant, summer*.—About 35 to 45 days at temperatures about 22° C. to 26° C.

*Root description*.—Thick, fibrous; typically close to N200A in color, actual color of the roots is dependent on substrate composition, water quality, fertilizers, substrate temperature and age of roots.

*Rooting habit*.—Moderately freely branching; medium density.

Plant description:

*Plant and growth habit*.—Perennial shrub; upright and strong flowering stems; typically grown as a standard type cut rose; moderately vigorous growth habit and moderate growth rate.

*Productivity*.—Plants of the new Rose are highly productive with about 11.52 flowering stems developing per plant per year; typical cut flower stem length is 60 cm to 70 cm.

*Plant height*.—About 152 cm.

*Plant width (spread)*.—About 34.8 cm.

*Lateral branches*.—Length: About 126 cm. Diameter: About 5 mm. Internode length: About 4.9 cm. Texture and luster: Smooth, glabrous; semi-glossy. Strength: Moderately strong. Color, developing: Close to 146A tinged with close to 166A. Color, developed: Close to 147A tinged with close to 200A; at the internodes, close to 200B. Thorns: Density: About two to three thorns per linear centimeter. Height: About 7.2 mm. Length, at base: About 7 mm. Shape: Deltoid; slightly incurved with sharp acute apices. Color, immature: Close to N148A. Color, mature: Close to 183A.

Leaf description:

*Arrangement*.—Alternate; compound with typically five to seven leaflets per leaf.

*Leaf length*.—About 16.1 cm.

*Leaf width*.—About 12.7 cm.

*Leaflet length*.—About 6.5 cm.

*Leaflet width*.—About 3.7 cm.

*Leaflet shape*.—Ovate.

*Leaflet apex*.—Acuminate.

*Leaflet base*.—Obtuse.

*Leaflet margin*.—Serrate.

*Leaflet texture and luster, upper surface*.—Smooth, glabrous; glossy.

*Leaflet texture and luster, lower surface*.—Smooth, glabrous; matte.

*Leaflet venation pattern*.—Pinnate and arcuate.

*Leaflet color*.—Developing leaflets, upper surface: Close to N77A. Developing leaflets, lower surface: Close to between 176A and 177A. Fully expanded leaflets, upper surface: Close to NN137A; venation, close to 183B. Fully expanded leaflets, lower surface: Close to 147B; venation, close to 152A.

*Petioles*.—Length: About 2 cm. Diameter: About 1.7 mm. Strength: Moderately strong. Texture and luster, upper surface: Slightly hirsutulous; matte. Texture and luster, lower surface: Smooth, glabrous; semi-glossy. Color, upper surface: Close to 146C. Color, lower surface: Close to 146A.

*Stipules*.—Arrangement and appearance: Two, adnate to the petiole, scale-like in appearance with acute apices and tapering towards the base; margins, ciliate. Length: About 2 cm. Width: About 2.1 mm. Texture and luster, upper and lower surfaces: Smooth, glabrous; membranous; matte. Venation pattern: Pinnate and arcuate. Color, upper surface: Close to NN137A. Color, lower surface: Close to 147B.

Flower description:

*Flower type and arrangement*.—Symmetrical rosette flowers; flowers typically grown as standard types with one terminal flower per flowering stem; flowers face upright.

*Flowering season*.—Plants of the new Rose flower year-round under greenhouse conditions in Ecuador; plants begin flowering about 85 to 90 days after planting young plants.

*Flower diameter*.—About 12.3 cm.

*Flower depth* (*height*).—About 6.8 cm.

*Flower longevity*.—Excellent postproduction longevity; flowers maintain good substance for about 43 days on the plant and as a cut flower, about six to eleven days; flowers persistent.

*Fragrance*.—None detected.

*Flower buds*.—Length: About 5.9 cm. Diameter: About 4.5 cm. Shape: Ovoid. Texture and luster: Smooth, glabrous; matte. Color: Close to 38B; towards the base, close to 7D.

*Petals*.—Quantity: About 38 to 45 per flower in about six whorls; petals imbricate, but not fused. Length: About 6.5 cm. Width: About 6.7 cm. Shape: Transverse elliptic. Apex: Rounded. Base: Rounded. Margin: Entire; slightly undulate. Texture and luster, upper surface: Slightly rugose, glabrous; matte. Texture and luster, lower surface: Smooth, glabrous; matte. Color: When opening, upper surface: Close to 51C; at the base, close to 33D. When opening, lower surface: Close to 37A; at the base, close to 33D. Fully opened, upper surface: Close to 62D; at the base, close to 22C. Fully opened, lower surface: Close to 62D; at the base, close to 23D.

*Petaloids*.—Quantity: About four to eleven in a single whorl; size and shape are variable. Length: About 2.6 cm. Width: About 1.7 cm. Texture and luster, upper and lower surfaces: Somewhat rugose, glabrous; matte. Color: when opening, upper and lower surfaces: Close to 48B; at the base, close to 12B. Fully opened, upper surface: Close to 39C; at the base, close to 13C. Fully opened, lower surface: Close to 39D; at the base, close to 13C.

*Sepals*.—Quantity per flower: Typically five in a single whorl. Length: About 4.1 cm. Width: About 1.2 cm. Shape: Lanceolate. Apex: Acuminate. Base: Truncate. Margin: Entire; slightly ciliolate. Texture and luster, upper surface: Slightly hirsute; matte. Texture and luster, lower surface: Hirsute; matte. Color: When opening, upper surface: Close to 144A. When opening, lower surface: Close to 146B. Fully opened, upper surface: Close to 143A. Fully opened, lower surface: Close to 146A.

*Reproductive organs*.—Stamens: Quantity: About 114 to 139 per flower. Filament length: About 8.7 mm. Filament color: Close to 28A. Anther size: About 2 mm by 4 mm. Anther shape: Reniform. Anther color: Close to 18A. Pollen amount: Moderate. Pollen color: Close to 18A. Pistils: Quantity: About 114 to 138 per flower. Pistil length: About 2.2 cm. Stigma diameter: About 0.9 mm. Stigma shape: Lobed. Stigma color: Close to 162B. Style length: About 1.2 cm. Style color: Close to 60A. Ovary color: Close to 155A. Receptacle height: About 5.7 mm. Receptacle diameter: About 1 cm. Receptacle shape: Cup-shaped. Receptacle texture: Slightly hirsute. Receptacle color: Close to between 139C to 137D. Fruits and seeds: To date, fruit and seed development have not been observed on plants of the new Rose.

Pathogen & pest tolerance: To date, plants of the new Rose have not been observed to be tolerant to pathogens and pests common to Rose plants.

It is claimed:

1. A new and distinct Rose plant named 'ESM R895' as herein illustrated and described.

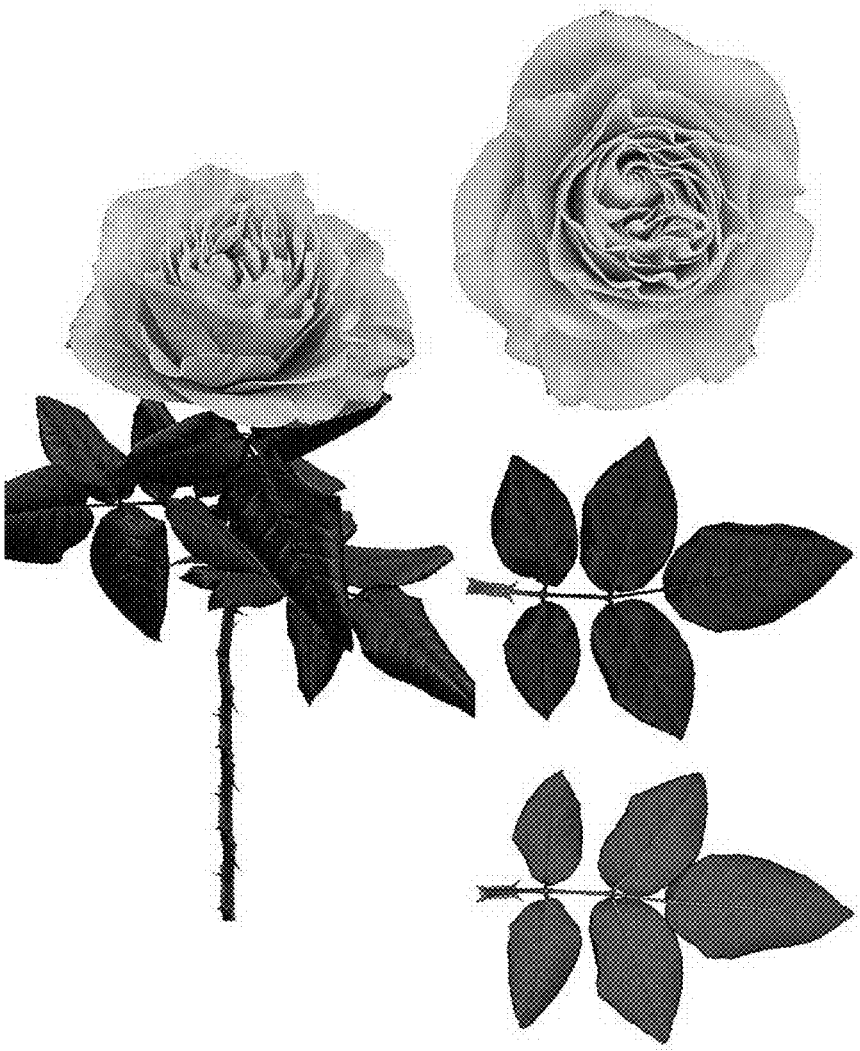

* * * * *